(12) United States Patent
Lord (10) Patent No.: US 11,701,482 B2
(45) Date of Patent: *Jul. 18, 2023

(54) ELECTRONIC INHALATION DEVICE (71) Applicant: NICOVENTURES TRADING LIMITED, London (GB)

(72) Inventor: Christopher Lord, London (GB)

(73) Assignee: Nicoventures Trading Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/247,498

(22) Filed: Dec. 14, 2020

(65) Prior Publication Data

US 2021/0093015 A1 Apr. 1, 2021

Related U.S. Application Data (63) Continuation of application No. 16/454,127, filed on Jun. 27, 2019, now Pat. No. 10,874,149, which is a
(Continued)

(30) Foreign Application Priority Data

Oct. 19, 2012 (GB) ...................................... 1218820

(51) Int. Cl.
*H01R 13/62* (2006.01)
*A61M 15/06* (2006.01)
(Continued)

(52) U.S. Cl.
CPC .............. *A61M 15/06* (2013.01); *A24F 40/53* (2020.01); *A24F 40/60* (2020.01); *A24F 40/65* (2020.01);
(Continued)

(58) Field of Classification Search
CPC ................ A61M 15/06; A61M 11/042; A61M 2016/0027; A61M 2205/3569;
(Continued)

(56) References Cited

U.S. PATENT DOCUMENTS

| 947,999 A | 2/1910 | Schweppe |
|---|---|---|
| 2,057,353 A | 10/1936 | Whittemore |

(Continued)

FOREIGN PATENT DOCUMENTS

| CA | 2641869 A1 | 5/2010 |
|---|---|---|
| CA | 2876267 A1 | 6/2015 |

(Continued)

OTHER PUBLICATIONS

Application and File History for U.S. Appl. No. 15/764,213, filed Mar. 28, 2018, Inventors: Baker et al, 174 pages.

(Continued)

*Primary Examiner* — Abdullah A Riyami
*Assistant Examiner* — Vladimir Imas
(74) *Attorney, Agent, or Firm* — Patterson Thuente, P.A.

(57) ABSTRACT

An electronic inhalation device comprising a mouthpiece and a control unit, the control unit comprising a power cell and a computer, where the computer comprises a computer processor, a memory and an input-output means; wherein the device further comprises a transmitter connected to the computer and the computer is configured in use to collect and store use data relating to a user's use of the device in the computer memory and transmit the use data.

17 Claims, 5 Drawing Sheets

Related U.S. Application Data continuation of application No. 14/432,750, filed as application No. PCT/EP2013/071072 on Oct. 9, 2013, now Pat. No. 10,375,990.

(51) Int. Cl.

| | | |
|---|---|---|
| *A24F 40/60* | (2020.01) | |
| *A24F 40/53* | (2020.01) | |
| *A24F 40/65* | (2020.01) | |
| *F22B 1/28* | (2006.01) | |
| *H04W 8/24* | (2009.01) | |
| *A61M 16/00* | (2006.01) | |
| *A61M 11/04* | (2006.01) | |
| *A24F 40/10* | (2020.01) | |

(52) U.S. Cl.
CPC ............... *F22B 1/284* (2013.01); *H04W 8/24* (2013.01); *A24F 40/10* (2020.01); *A61M 11/042* (2014.02); *A61M 2016/0027* (2013.01); *A61M 2205/3375* (2013.01); *A61M 2205/3569* (2013.01); *A61M 2205/3592* (2013.01); *A61M 2205/52* (2013.01); *A61M 2205/8206* (2013.01)

(58) Field of Classification Search
CPC ...... A61M 2205/3592; A61M 2205/52; A61M 2205/8206; A61M 2205/3375; F22B 1/284; A24F 40/60; A24F 40/53; A24F 40/65; A24F 40/10; H04W 8/24
USPC .......................................................... 439/328
See application file for complete search history.

(56) References Cited

U.S. PATENT DOCUMENTS

| | | | |
|---|---|---|---|
| 3,200,819 A | 8/1965 | Gilbert | |
| 4,358,665 A | 11/1982 | Owen | |
| 4,523,084 A | 6/1985 | Tamura et al. | |
| 4,907,606 A | 3/1990 | Lilja et al. | |
| 4,947,874 A | 8/1990 | Brooks et al. | |
| 4,947,875 A | 8/1990 | Brooks et al. | |
| 4,986,269 A | 1/1991 | Hakkinen | |
| 5,027,837 A | 7/1991 | Clearman et al. | |
| 5,095,921 A | 3/1992 | Losee et al. | |
| 5,261,424 A | 11/1993 | Sprinkel, Jr. | |
| 5,331,953 A | 7/1994 | Andersson et al. | |
| 5,363,842 A | 11/1994 | Mishelevich et al. | |
| 5,372,148 A | 12/1994 | McCafferty et al. | |
| 5,434,386 A | 7/1995 | Glenn et al. | |
| 5,613,505 A | 3/1997 | Campbell et al. | |
| 5,808,881 A | 9/1998 | Lee | |
| 5,809,997 A | 9/1998 | Wolf | |
| 5,878,752 A | 3/1999 | Adams et al. | |
| 5,894,841 A | 4/1999 | Voges | |
| 5,949,632 A | 9/1999 | Barreras, Sr. et al. | |
| 6,040,560 A | 3/2000 | Fleischhauer et al. | |
| 6,183,425 B1 | 2/2001 | Whalen et al. | |
| 6,196,218 B1 | 3/2001 | Voges | |
| 6,370,339 B1 | 4/2002 | Stern et al. | |
| 6,435,175 B1 | 8/2002 | Stenzler | |
| 6,540,672 B1 | 4/2003 | Simonsen et al. | |
| 6,615,825 B2 | 9/2003 | Stenzler | |
| 6,615,840 B1 | 9/2003 | Fournier et al. | |
| 6,729,327 B2 | 5/2004 | McFarland, Jr. | |
| 6,766,220 B2 | 7/2004 | McRae et al. | |
| 6,814,083 B2 | 11/2004 | Likness et al. | |
| 6,873,322 B2 | 3/2005 | Hartular | |
| 6,958,691 B1 | 10/2005 | Anderson et al. | |
| 7,109,445 B2 | 9/2006 | Patterson et al. | |
| 7,147,170 B2 | 12/2006 | Nguyen et al. | |
| 7,547,285 B2 | 6/2009 | Kline | |
| 7,726,320 B2 | 6/2010 | Robinson et al. | |
| 7,726,329 B2 | 6/2010 | Armiroli et al. | |
| 7,849,851 B2 | 12/2010 | Zierenberg et al. | |
| 8,079,371 B2 | 12/2011 | Robinson et al. | |
| 8,159,204 B2 | 4/2012 | Grant | |
| 8,357,114 B2 * | 1/2013 | Poutiatine | A61J 7/0481 |
| | | | 604/59 |
| 8,453,601 B2 | 6/2013 | Zimmerman | |
| 8,511,304 B2 | 8/2013 | Anderson et al. | |
| 8,550,068 B2 | 10/2013 | Terry et al. | |
| 8,550,069 B2 | 10/2013 | Alelov | |
| 8,631,791 B2 | 1/2014 | Bordewick et al. | |
| 8,746,240 B2 | 6/2014 | Terry et al. | |
| 8,757,147 B2 | 6/2014 | Terry et al. | |
| 8,807,131 B1 | 8/2014 | Tunnell et al. | |
| 8,997,753 B2 | 4/2015 | Li et al. | |
| 9,095,175 B2 | 8/2015 | Terry et al. | |
| 9,289,014 B2 | 3/2016 | Tucker et al. | |
| 9,352,108 B1 | 5/2016 | Reed et al. | |
| 9,362,048 B2 | 6/2016 | Yamamoto | |
| 9,439,455 B2 | 9/2016 | Alarcon et al. | |
| 9,451,791 B2 | 9/2016 | Sears et al. | |
| 9,462,832 B2 | 10/2016 | Lord | |
| 9,497,999 B2 | 11/2016 | Lord | |
| 9,597,466 B2 | 3/2017 | Henry, Jr. et al. | |
| 9,724,482 B2 | 8/2017 | Bach et al. | |
| 9,782,551 B2 | 10/2017 | Morrison et al. | |
| 10,065,138 B2 | 9/2018 | Blackley | |
| 10,117,460 B2 | 11/2018 | Sears et al. | |
| 10,159,279 B2 | 12/2018 | Lord et al. | |
| 10,334,885 B2 | 7/2019 | Baker et al. | |
| 10,375,990 B2 * | 8/2019 | Lord | A24F 40/65 |
| 10,477,893 B2 | 11/2019 | Lord | |
| 2002/0000225 A1 | 1/2002 | Schuler et al. | |
| 2003/0033055 A1 | 2/2003 | McRae et al. | |
| 2003/0033067 A1 | 2/2003 | Arita et al. | |
| 2003/0051181 A1 | 3/2003 | Magee et al. | |
| 2003/0123328 A1 | 7/2003 | Guanter | |
| 2003/0123329 A1 | 7/2003 | Guanter et al. | |
| 2003/0179003 A1 | 9/2003 | Toda et al. | |
| 2003/0212549 A1 | 11/2003 | Steentra et al. | |
| 2003/0226837 A1 | 12/2003 | Blake et al. | |
| 2004/0081624 A1 | 4/2004 | Nguyen et al. | |
| 2005/0045193 A1 | 3/2005 | Yang | |
| 2005/0058441 A1 | 3/2005 | Kameyama et al. | |
| 2005/0081846 A1 | 4/2005 | Barney | |
| 2005/0143866 A1 | 6/2005 | McRae et al. | |
| 2005/0161467 A1 | 7/2005 | Jones | |
| 2005/0247305 A1 | 11/2005 | Zierenberg et al. | |
| 2005/0268911 A1 | 12/2005 | Cross et al. | |
| 2005/0274193 A1 | 12/2005 | Kwon et al. | |
| 2006/0047368 A1 | 3/2006 | Maharajh et al. | |
| 2006/0090087 A1 | 4/2006 | Oh et al. | |
| 2006/0100002 A1 | 5/2006 | Luebke et al. | |
| 2006/0130838 A1 | 6/2006 | Lee et al. | |
| 2006/0130860 A1 * | 6/2006 | Cholet | A24F 13/12 |
| | | | 131/330 |
| 2006/0240798 A1 | 10/2006 | Jarosinski et al. | |
| 2007/0006889 A1 | 1/2007 | Kobal | |
| 2007/0014314 A1 | 1/2007 | O'Neil | |
| 2007/0027994 A1 | 2/2007 | Arai et al. | |
| 2007/0029969 A1 | 2/2007 | Wang et al. | |
| 2007/0037610 A1 | 2/2007 | Logan | |
| 2007/0045288 A1 | 3/2007 | Nelson | |
| 2007/0074734 A1 | 4/2007 | Braunshteyn et al. | |
| 2007/0113665 A1 | 5/2007 | Johnson | |
| 2007/0162772 A1 | 7/2007 | Huang et al. | |
| 2007/0186923 A1 | 8/2007 | Poutiatine et al. | |
| 2007/0225587 A1 | 9/2007 | Burnell et al. | |
| 2007/0267031 A1 | 11/2007 | Hon | |
| 2008/0092912 A1 | 4/2008 | Robinson et al. | |
| 2008/0194268 A1 | 8/2008 | Koch | |
| 2008/0257367 A1 * | 10/2008 | Paterno | A61M 15/06 |
| | | | 131/194 |
| 2008/0272836 A1 | 11/2008 | Smit et al. | |
| 2008/0276050 A1 | 11/2008 | Hsieh et al. | |
| 2009/0095287 A1 * | 4/2009 | Emarlou | A61M 15/06 |
| | | | 128/200.14 |
| 2009/0095311 A1 | 4/2009 | Han | |
| 2009/0095312 A1 | 4/2009 | Herbrich et al. | |
| 2009/0230117 A1 | 9/2009 | Fernando et al. | |

(56) References Cited

U.S. PATENT DOCUMENTS

| | | |
|---|---|---|
| 2009/0283103 A1 | 11/2009 | Nielsen et al. |
| 2009/0308387 A1 | 12/2009 | Andersen et al. |
| 2010/0024517 A1 | 2/2010 | Ratner |
| 2010/0050770 A1 | 3/2010 | Barger et al. |
| 2010/0059070 A1 | 3/2010 | Potter et al. |
| 2010/0084918 A1 | 4/2010 | Fells et al. |
| 2010/0157095 A1 | 6/2010 | Karn et al. |
| 2010/0163063 A1 | 7/2010 | Fernando et al. |
| 2010/0206306 A1 | 8/2010 | Feriani et al. |
| 2010/0236546 A1 | 9/2010 | Kamada et al. |
| 2010/0242974 A1 | 9/2010 | Pan |
| 2010/0243674 A1 | 9/2010 | Furner et al. |
| 2010/0250280 A1 | 9/2010 | Sutherland |
| 2010/0252036 A1 | 10/2010 | Sutherland et al. |
| 2011/0036346 A1* | 2/2011 | Cohen ............... A24F 40/60 128/200.14 |
| 2011/0110746 A1 | 5/2011 | Smith |
| 2011/0113368 A1 | 5/2011 | Carvajal et al. |
| 2011/0210746 A1 | 9/2011 | Yugou et al. |
| 2011/0226236 A1 | 9/2011 | Buchberger |
| 2011/0247620 A1 | 10/2011 | Armstrong et al. |
| 2011/0253139 A1 | 10/2011 | Guthrie et al. |
| 2011/0265806 A1* | 11/2011 | Alarcon ............. A24F 40/485 131/273 |
| 2011/0277756 A1 | 11/2011 | Terry et al. |
| 2011/0277760 A1 | 11/2011 | Terry et al. |
| 2011/0277764 A1 | 11/2011 | Terry et al. |
| 2011/0278189 A1 | 11/2011 | Terry et al. |
| 2011/0304282 A1 | 12/2011 | Li et al. |
| 2012/0012106 A1 | 1/2012 | Bari |
| 2012/0048266 A1 | 3/2012 | Alelov |
| 2012/0060853 A1 | 3/2012 | Robinson et al. |
| 2012/0134238 A1 | 5/2012 | Surprenant et al. |
| 2012/0186594 A1 | 7/2012 | Liu |
| 2012/0208601 A1 | 8/2012 | Lockwood |
| 2012/0214107 A1 | 8/2012 | Al Gharib |
| 2012/0227752 A1* | 9/2012 | Alelov ............... A24F 40/51 131/273 |
| 2012/0234821 A1 | 9/2012 | Shimizu |
| 2012/0242974 A1 | 9/2012 | LaValley et al. |
| 2012/0298220 A1 | 11/2012 | Hidaka et al. |
| 2012/0318882 A1 | 12/2012 | Abehasera |
| 2012/0325227 A1 | 12/2012 | Robinson et al. |
| 2013/0008436 A1 | 1/2013 | Von Hollen et al. |
| 2013/0027089 A1 | 1/2013 | Huang |
| 2013/0042865 A1 | 2/2013 | Monsees et al. |
| 2013/0091452 A1 | 4/2013 | Sorden et al. |
| 2013/0104916 A1 | 5/2013 | Bellinger et al. |
| 2013/0113388 A1 | 5/2013 | Reams |
| 2013/0192615 A1 | 8/2013 | Tucker et al. |
| 2013/0192622 A1 | 8/2013 | Tucker et al. |
| 2013/0199528 A1 | 8/2013 | Goodman et al. |
| 2013/0220315 A1 | 8/2013 | Conley et al. |
| 2013/0228191 A1 | 9/2013 | Newton |
| 2013/0255702 A1 | 10/2013 | Griffith, Jr. et al. |
| 2013/0269685 A1 | 10/2013 | Wachtel et al. |
| 2013/0276799 A1 | 10/2013 | Davidson et al. |
| 2013/0284192 A1 | 10/2013 | Peleg et al. |
| 2013/0319439 A1 | 12/2013 | Gorelick et al. |
| 2013/0319989 A1 | 12/2013 | Liu |
| 2013/0340755 A1 | 12/2013 | Ruff |
| 2013/0340775 A1 | 12/2013 | Juster et al. |
| 2014/0000603 A1 | 1/2014 | Hosemann et al. |
| 2014/0000638 A1 | 1/2014 | Sebastian et al. |
| 2014/0007892 A1 | 1/2014 | Liu |
| 2014/0008384 A1 | 1/2014 | Helmlinger |
| 2014/0014126 A1 | 1/2014 | Peleg et al. |
| 2014/0060552 A1 | 3/2014 | Cohen |
| 2014/0060554 A1 | 3/2014 | Collett et al. |
| 2014/0096781 A1 | 4/2014 | Sears et al. |
| 2014/0123990 A1 | 5/2014 | Timmermans |
| 2014/0174459 A1 | 6/2014 | Burstyn |
| 2014/0202477 A1 | 7/2014 | Qi et al. |
| 2014/0209105 A1 | 7/2014 | Sears et al. |
| 2014/0246035 A1 | 9/2014 | Minskoff et al. |
| 2014/0261414 A1 | 9/2014 | Weitzel et al. |
| 2014/0261486 A1 | 9/2014 | Potter et al. |
| 2014/0270727 A1 | 9/2014 | Ampolini et al. |
| 2014/0299125 A1 | 10/2014 | Buchberger |
| 2014/0321837 A1 | 10/2014 | Flick |
| 2014/0345635 A1 | 11/2014 | Rabinowitz et al. |
| 2014/0366894 A1 | 12/2014 | Liu |
| 2014/0366898 A1 | 12/2014 | Monsees et al. |
| 2015/0047656 A1 | 2/2015 | Robinson et al. |
| 2015/0075546 A1 | 3/2015 | Kueny, Sr. et al. |
| 2015/0097513 A1 | 4/2015 | Liberti et al. |
| 2015/0101625 A1 | 4/2015 | Newton et al. |
| 2015/0114408 A1 | 4/2015 | Lord |
| 2015/0128965 A1 | 5/2015 | Lord |
| 2015/0128966 A1 | 5/2015 | Lord |
| 2015/0136153 A1 | 5/2015 | Lord |
| 2015/0173124 A1 | 6/2015 | Qiu |
| 2015/0174348 A1 | 6/2015 | Tunnell et al. |
| 2015/0181945 A1 | 7/2015 | Tremblay |
| 2015/0208723 A1 | 7/2015 | Glazer |
| 2015/0237917 A1 | 8/2015 | Lord |
| 2015/0245660 A1 | 9/2015 | Lord |
| 2015/0257448 A1 | 9/2015 | Lord |
| 2015/0289565 A1 | 10/2015 | Cadieux et al. |
| 2015/0336689 A1 | 11/2015 | Brown et al. |
| 2015/0338235 A1 | 11/2015 | Schmidt et al. |
| 2016/0021930 A1 | 1/2016 | Minskoff et al. |
| 2016/0206000 A1 | 7/2016 | Lord et al. |
| 2016/0218656 A1 | 7/2016 | Hawliczek et al. |
| 2016/0242466 A1 | 8/2016 | Lord et al. |
| 2016/0255878 A1 | 9/2016 | Huang et al. |
| 2016/0278435 A1 | 9/2016 | Choukroun et al. |
| 2016/0295913 A1 | 10/2016 | Guo et al. |
| 2016/0337141 A1 | 11/2016 | Cameron |
| 2016/0339188 A1 | 11/2016 | Flickinger |
| 2017/0035114 A1 | 2/2017 | Lord |
| 2017/0035144 A1 | 2/2017 | Parker |
| 2017/0048691 A1 | 2/2017 | Liu |
| 2017/0055583 A1 | 3/2017 | Blandino et al. |
| 2017/0118292 A1 | 4/2017 | Xiang |
| 2017/0118584 A1 | 4/2017 | Xiang |
| 2017/0245547 A1 | 8/2017 | Lipowicz |
| 2017/0340016 A1 | 11/2017 | Thorens |
| 2017/0340017 A1 | 11/2017 | Thorens |
| 2018/0007972 A1 | 1/2018 | Thorens |
| 2018/0153223 A1 | 6/2018 | Lord |
| 2018/0192700 A1 | 7/2018 | Fraser et al. |
| 2018/0214645 A1 | 8/2018 | Reevell |
| 2018/0242642 A1 | 8/2018 | Silvesstrini et al. |
| 2018/0271155 A1 | 9/2018 | Baker et al. |
| 2018/0279681 A1 | 10/2018 | Rojo-Calderon et al. |
| 2018/0280640 A1 | 10/2018 | Baker et al. |
| 2018/0303163 A1 | 10/2018 | Baker et al. |
| 2018/0310623 A1 | 11/2018 | Batista |
| 2019/0133192 A1 | 5/2019 | Lord et al. |
| 2019/0380391 A1 | 12/2019 | Reevell |
| 2020/0000148 A1 | 1/2020 | Horrod et al. |
| 2020/0022412 A1 | 1/2020 | Abi Aoun et al. |
| 2020/0037402 A1 | 1/2020 | Abi Aoun et al. |
| 2020/0138109 A1 | 5/2020 | Lord |
| 2020/0163384 A1 | 5/2020 | Rossoll et al. |
| 2020/0214350 A1 | 7/2020 | Courbat et al. |
| 2020/0221772 A1 | 7/2020 | Mironov et al. |
| 2021/0345681 A1 | 11/2021 | Cameron |
| 2022/0183368 A1 | 6/2022 | Abi Aoun et al. |
| 2022/0291930 A1 | 9/2022 | Litvinov et al. |

FOREIGN PATENT DOCUMENTS

| | | |
|---|---|---|
| CN | 1224322 A | 7/1999 |
| CN | 1280661 A | 1/2001 |
| CN | 1330427 A | 1/2002 |
| CN | 1330563 A | 1/2002 |
| CN | 1428671 A | 7/2003 |
| CN | 1500546 A | 6/2004 |
| CN | 1635920 A | 7/2005 |
| CN | 1812529 A | 8/2006 |
| CN | 200983833 Y | 12/2007 |
| CN | 201029436 Y | 3/2008 |

(56) References Cited

FOREIGN PATENT DOCUMENTS

| | | | |
|---|---|---|---|
| CN | 201061262 Y | 5/2008 |
| CN | 201104488 Y | 8/2008 |
| CN | 201188352 Y | 1/2009 |
| CN | 201238610 Y | 5/2009 |
| CN | 101518361 A | 9/2009 |
| CN | 101522244 A | 9/2009 |
| CN | 101524187 A | 9/2009 |
| CN | 201312137 Y | 9/2009 |
| CN | 101557728 A | 10/2009 |
| CN | 100566769 C | 12/2009 |
| CN | 201379072 Y | 1/2010 |
| CN | 201393548 Y | 2/2010 |
| CN | 101813963 A | 8/2010 |
| CN | 101970020 A | 2/2011 |
| CN | 201821914 U | 5/2011 |
| CN | 201830899 U | 5/2011 |
| CN | 102143339 A | 8/2011 |
| CN | 102218180 A | 10/2011 |
| CN | 102247640 A | 11/2011 |
| CN | 102264251 A | 11/2011 |
| CN | 102322893 A | 1/2012 |
| CN | 102350061 A | 2/2012 |
| CN | 102375525 A | 3/2012 |
| CN | 202364801 U | 8/2012 |
| CN | 102759655 A | 10/2012 |
| CN | 102934843 A | 2/2013 |
| CN | 102970885 A | 3/2013 |
| CN | 202890466 U | 4/2013 |
| CN | 203070141 U | 7/2013 |
| CN | 103237468 A | 8/2013 |
| CN | 102218180 B | 11/2013 |
| CN | 103415222 A | 11/2013 |
| CN | 103798960 A | 5/2014 |
| CN | 104049550 A | 9/2014 |
| CN | 203841114 U | 9/2014 |
| CN | 203913385 U | 11/2014 |
| CN | 203952405 U | 11/2014 |
| CN | 203986103 U | 12/2014 |
| CN | 104464237 A | 3/2015 |
| CN | 104540406 A | 4/2015 |
| CN | 104544570 A | 4/2015 |
| CN | 204335831 U | 5/2015 |
| CN | 107949288 A | 4/2018 |
| CN | 108348004 A | 7/2018 |
| CN | 108783613 A | 11/2018 |
| CN | 109330030 A | 2/2019 |
| DE | 102009029768 A1 | 1/2011 |
| DE | 102009035973 A1 | 4/2011 |
| EA | 019736 B1 | 5/2014 |
| EP | 0430559 A2 | 6/1991 |
| EP | 0628336 A1 | 12/1994 |
| EP | 0701195 A1 | 3/1996 |
| EP | 0874302 A1 | 10/1998 |
| EP | 0924593 A2 | 6/1999 |
| EP | 1036289 A1 | 9/2000 |
| EP | 1111527 A2 | 6/2001 |
| EP | 1494407 A1 | 1/2005 |
| EP | 1565015 A2 | 8/2005 |
| EP | 1712178 A2 | 10/2006 |
| EP | 1785711 A2 | 5/2007 |
| EP | 1989946 A1 | 11/2008 |
| EP | 2047880 A1 | 4/2009 |
| EP | 2110034 A1 | 10/2009 |
| EP | 2119375 A1 | 11/2009 |
| EP | 2143346 A1 | 1/2010 |
| EP | 2292108 A1 | 3/2011 |
| EP | 2340730 A1 | 7/2011 |
| EP | 2404515 A1 | 1/2012 |
| EP | 2460423 A1 | 6/2012 |
| EP | 2468118 A1 | 6/2012 |
| EP | 2727619 A2 | 5/2014 |
| EP | 2908673 A2 | 8/2015 |
| EP | 2908675 A1 | 8/2015 |
| EP | 3116334 A1 | 1/2017 |
| EP | 3154382 A1 | 4/2017 |
| EP | 3307097 A1 | 4/2018 |
| EP | 2414978 B1 | 12/2018 |
| EP | 2908675 B1 | 1/2019 |
| EP | 3054798 B1 | 5/2019 |
| EP | 3316711 B1 | 5/2019 |
| EP | 3636084 A1 | 4/2020 |
| ES | 1091555 U | 10/2013 |
| GB | 2468932 A | 9/2010 |
| GB | 2502053 A | 11/2013 |
| GB | 2502055 A | 11/2013 |
| GB | 2502162 A | 11/2013 |
| GB | 2502163 A | 11/2013 |
| GB | 2502164 A | 11/2013 |
| GB | 2507103 A | 4/2014 |
| GB | 2507104 A | 4/2014 |
| GB | 2514767 A | 12/2014 |
| GB | 2519101 A | 4/2015 |
| GB | 2519317 A | 4/2015 |
| GB | 2507102 B | 12/2015 |
| JP | S5640917 A | 4/1981 |
| JP | H02124082 A | 5/1990 |
| JP | H05212100 A | 8/1993 |
| JP | H069233 U | 2/1994 |
| JP | H07506008 A | 7/1995 |
| JP | H08511966 A | 12/1996 |
| JP | H11002577 | 1/1999 |
| JP | 2000132654 A | 5/2000 |
| JP | 2000330844 A | 11/2000 |
| JP | 2001502542 A | 2/2001 |
| JP | 3392138 B2 | 3/2003 |
| JP | 2004177579 A | 6/2004 |
| JP | 3696619 B2 | 9/2005 |
| JP | 2005538159 A | 12/2005 |
| JP | 2006018057 A | 1/2006 |
| JP | 2006507499 A | 3/2006 |
| JP | 2006338178 A | 12/2006 |
| JP | 2007034596 A | 2/2007 |
| JP | 2007192802 A | 8/2007 |
| JP | 3976345 B2 | 9/2007 |
| JP | 2008064932 A | 3/2008 |
| JP | 2008165769 A | 7/2008 |
| JP | 2008309379 A | 12/2008 |
| JP | 2009022752 A | 2/2009 |
| JP | 2009525746 A | 7/2009 |
| JP | 3159830 U | 6/2010 |
| JP | 2010522584 A | 7/2010 |
| JP | 2010526553 A | 8/2010 |
| JP | 2012506263 A | 3/2012 |
| JP | 4933046 B2 | 5/2012 |
| JP | 2012104085 A | 5/2012 |
| JP | 2012135299 A | 7/2012 |
| JP | 5041550 B2 | 10/2012 |
| JP | 2013524835 A | 6/2013 |
| JP | 2013545474 A | 12/2013 |
| JP | 2014501106 A | 1/2014 |
| JP | 2014504886 A | 2/2014 |
| JP | 2014534814 A | 12/2014 |
| JP | 2015512262 A | 4/2015 |
| JP | 2015537195 A | 12/2015 |
| JP | 2016536957 A | 11/2016 |
| JP | 6352272 B2 | 7/2018 |
| JP | 2019186178 A | 10/2019 |
| KR | 100495099 B1 | 11/2005 |
| KR | 20110002227 U | 3/2011 |
| KR | 20110132290 A | 12/2011 |
| KR | 20120027029 A | 3/2012 |
| KR | 20120080477 A | 7/2012 |
| KR | 20120089544 A | 8/2012 |
| KR | 20120093046 A | 8/2012 |
| KR | 20120094400 A | 8/2012 |
| KR | 101256914 B1 | 4/2013 |
| RU | 1837815 A3 | 8/1993 |
| RU | 72821 U1 | 5/2008 |
| RU | 2336001 C2 | 10/2008 |
| RU | 2336002 C2 | 10/2008 |
| RU | 83387 U1 | 6/2009 |
| RU | 2360583 C1 | 7/2009 |
| RU | 94815 U1 | 6/2010 |
| RU | 107026 U1 | 8/2011 |

(56) References Cited

FOREIGN PATENT DOCUMENTS

| | | |
|---|---|---|
| RU | 2425608 C2 | 8/2011 |
| RU | 110608 U1 | 11/2011 |
| RU | 124120 U1 | 1/2013 |
| RU | 2509516 C2 | 3/2014 |
| SE | 9900703 L | 12/1999 |
| TW | 200928407 A | 7/2009 |
| UA | 90256 C2 | 4/2010 |
| UA | 92474 C2 | 11/2010 |
| UA | 67598 U | 2/2012 |
| UA | 100068 C2 | 11/2012 |
| UA | 100734 C2 | 1/2013 |
| UA | 78167 U | 3/2013 |
| UA | 102423 C2 | 7/2013 |
| WO | 9118860 A1 | 12/1991 |
| WO | 9418860 A1 | 9/1994 |
| WO | 9501137 A1 | 1/1995 |
| WO | 9520805 A1 | 8/1995 |
| WO | 9810603 A2 | 3/1998 |
| WO | 9817130 A1 | 4/1998 |
| WO | 9817131 A1 | 4/1998 |
| WO | 0050111 A1 | 8/2000 |
| WO | 0064517 A1 | 11/2000 |
| WO | 0157619 A2 | 8/2001 |
| WO | 03070031 A1 | 8/2003 |
| WO | 03095005 A1 | 11/2003 |
| WO | 2004080216 A1 | 9/2004 |
| WO | 2004095955 A1 | 11/2004 |
| WO | 2005060358 A2 | 7/2005 |
| WO | 2005063322 A2 | 7/2005 |
| WO | 2007091181 A2 | 8/2007 |
| WO | 2007103380 A2 | 9/2007 |
| WO | 2008014120 A2 | 1/2008 |
| WO | 2008139411 A2 | 11/2008 |
| WO | 2008142015 A2 | 11/2008 |
| WO | 2009045198 A1 | 4/2009 |
| WO | 2009063814 A1 | 5/2009 |
| WO | 2009069518 A1 | 6/2009 |
| WO | 2009118085 A1 | 10/2009 |
| WO | 2009134164 A1 | 11/2009 |
| WO | 2009146484 A1 | 12/2009 |
| WO | 2010003480 A1 | 1/2010 |
| WO | 2010045670 A1 | 4/2010 |
| WO | 2010073122 A1 | 7/2010 |
| WO | 2010091593 A1 | 8/2010 |
| WO | 2010110682 A1 | 9/2010 |
| WO | 2010114392 A1 | 10/2010 |
| WO | 2010118644 A1 | 10/2010 |
| WO | 2010145805 A1 | 12/2010 |
| WO | 2011033396 A2 | 3/2011 |
| WO | 2011056889 A1 | 5/2011 |
| WO | 2011067877 A1 | 6/2011 |
| WO | 2011079932 A1 | 7/2011 |
| WO | 2011137453 A2 | 11/2011 |
| WO | 2011147699 A1 | 12/2011 |
| WO | 2012027350 A2 | 3/2012 |
| WO | 2012048266 A1 | 4/2012 |
| WO | 2012072790 A1 | 6/2012 |
| WO | 2012109371 A2 | 8/2012 |
| WO | 2012117376 A1 | 9/2012 |
| WO | 2012120487 A2 | 9/2012 |
| WO | 2013060781 A1 | 5/2013 |
| WO | 2013060784 A2 | 5/2013 |
| WO | 2013060874 A1 | 5/2013 |
| WO | 2013098395 A1 | 7/2013 |
| WO | 2013098397 A2 | 7/2013 |
| WO | 2013098398 A2 | 7/2013 |
| WO | 2013116572 A1 | 8/2013 |
| WO | 2013138384 A2 | 9/2013 |
| WO | 2013148810 A1 | 10/2013 |
| WO | 2014004437 A1 | 1/2014 |
| WO | 2014037794 A2 | 3/2014 |
| WO | 2014054035 A1 | 4/2014 |
| WO | 2014060268 A1 | 4/2014 |
| WO | 2014060269 A1 | 4/2014 |
| WO | 2014111537 A1 | 7/2014 |
| WO | 2014150704 A2 | 9/2014 |
| WO | 2014195805 A2 | 12/2014 |
| WO | 2014199233 A2 | 12/2014 |
| WO | 2014205456 A2 | 12/2014 |
| WO | 2015051248 A1 | 4/2015 |
| WO | 2015052513 A2 | 4/2015 |
| WO | 2015063126 A1 | 5/2015 |
| WO | 2015112750 A1 | 7/2015 |
| WO | 2015138589 A1 | 9/2015 |
| WO | 2015149326 A1 | 10/2015 |
| WO | 2015161485 A1 | 10/2015 |
| WO | 2015175701 A1 | 11/2015 |
| WO | 2015192084 A1 | 12/2015 |
| WO | 2016008096 A1 | 1/2016 |
| WO | 2016009202 A1 | 1/2016 |
| WO | 2016198266 A1 | 12/2016 |
| WO | 2017001817 A1 | 1/2017 |
| WO | 2017068099 A1 | 4/2017 |
| WO | 2017153443 A1 | 9/2017 |
| WO | 2017186455 A1 | 11/2017 |
| WO | 2018073376 A1 | 4/2018 |
| WO | 2018099999 A1 | 6/2018 |
| WO | 2018178095 A1 | 10/2018 |
| WO | 2019030000 A1 | 2/2019 |
| WO | 2019030168 A1 | 2/2019 |
| WO | 2019030353 A1 | 2/2019 |
| WO | 2019030360 A1 | 2/2019 |
| WO | 2019030361 A1 | 2/2019 |
| WO | 2019030364 A1 | 2/2019 |
| WO | 2019129552 A1 | 7/2019 |
| WO | 2019129553 A1 | 7/2019 |
| WO | 2020025701 A1 | 2/2020 |
| WO | 2020025712 A1 | 2/2020 |
| WO | 2020025714 A1 | 2/2020 |
| WO | 2020025718 A1 | 2/2020 |
| WO | 2020025719 A1 | 2/2020 |
| WO | 2020025725 A1 | 2/2020 |
| WO | 2020025727 A1 | 2/2020 |
| WO | 2020025728 A1 | 2/2020 |
| WO | 2020025730 A1 | 2/2020 |
| WO | 2020025731 A1 | 2/2020 |
| WO | 2020035454 A1 | 2/2020 |
| WO | 2020064683 A1 | 4/2020 |
| WO | 2020064684 A1 | 4/2020 |
| WO | 2020064685 A1 | 4/2020 |
| WO | 2020064686 A1 | 4/2020 |
| WO | 2020120551 A1 | 6/2020 |

OTHER PUBLICATIONS

Application and File History for U.S. Appl. No. 16/272,187, filed Feb. 11, 2019, Inventor: Baker, 216 pages.

Chellis J., et al., "Foundations of the construction of networks. Manual for the professionals MCSE", "LORI", 1997, 8 pages.

Chellis J. et al., "MCSA / MCSE: Windows Server 2003 Network Infrastructure, Implementation, Management and Maintenance Study Guide: Exam 70-291," 2003, 7 pages.

Communication pursuant to Article 94(3) EPC For European Application No. 16770300.8, dated Sep. 24, 2020, 5 pages.

Decision dated Feb. 17, 2016 for Ukraine Application No. 201503483, 8 pages.

Erman D., "Design and Implementation of an Acoustical Transmission Protocol", Feb. 22, 2002, Master's Thesis MEE0126, Blenkinge Institute of Technology, 53 pages.

Examination Report dated Dec. 4, 2015 for Application No. 2013331850, 4 pages.

Fan, et al., "Development and research of temporary demand pacemaker with electrocardiosignal display." Journal of biomedical engineering 21.4, 2004, pp. 650-653.

Graf R. F., "Modern Dictionary of Electronics," Seventh Edition, 1999, 9 pages.

Igoe T, "Making Things Talk: Practical Methods for Connecting Physical Objects;"O'Reilly Media, Inc, Sep. 28, 2007, 33 pages.

Illinguort, "Explanatory dictionary of computing systems", Machine-building, 1990, 4 pages.

(56) References Cited

OTHER PUBLICATIONS

International Preliminary Report on Patentability for Application No. PCT/EP2013/071072, dated Apr. 21, 2015, 6 pages.
International Search Report for Application No. PCT/EP2013/071072 dated Mar. 24, 2014, 4 pages.
Mostitsky I.L., "English-Russian encyclopedic dictionary of the modern electronic technology and programming: computers, internet, telecommunications, audio-, video-, tele-, radio-technology etc .," Moscow Triumph Publishing House , 2004, 4 pages.
"New Progress in Modern Technical Theory and Practice of Underground Mining—A Collection of Theses for Celebrating 50th Anniversary of Beijing Institute of Exploitation under Coal Research Headquarter," Beijing Institute of Exploitation under Coal Research Headquarter, May 2007, p. 318.
Notice of Final Rejection dated Jun. 1, 2017 for Korean Application No. 10-2015-7010073, 5 pages.
Notice Of Reason for Refusal for Japanese Application No. 2018-108247 dated Apr. 27, 2021, 8 pages.
Notice Of Reason for Refusal for Japanese Application No. 2018-108247 dated Aug. 27, 2019, 8 pages.
Notice to File a Response dated Oct. 19, 2016 for Korean Application No. 10-2015-7010073, 28 pages.
Notification of Reasons for Refusal dated Feb. 20, 2017 for Korean Application No. 10-2015-7010073, 9 pages.
Observations Under Article 115 EPC Relating to European Application No. 13777004.6, dated Nov. 20, 2018, 16 pages.
Office Action and Search Report for Chinese Application No. 201380054490.7, dated Oct. 9, 2017, 16 pages.
Office Action for Chinese Application No. 201380054490.7, dated May 18, 2018, 14 pages.
Office Action for Japanese Application No. 2015-537197, dated Jul. 18, 2017, 6 pages.
Office Action for Japanese Application No. 2018-515461, dated Jan. 8, 2019, 8 pages.
Office Action For Japanese Application No. 2020-143411, dated Nov. 9, 2021, 6 pages.
Office Action For Korean Application No. 10-2021-7024336, dated Sep. 7, 2021, 19 pages.
Office Action dated Apr. 25, 2019 for Korean Application No. 10-2017-7018345, 14 pages (27 pages with translation).
Office Action dated Oct. 19, 2018 for Korean Application No. 10-2017-7018345, 10 pages (22 pages with translation).
Russian Nullity dated Jun. 20, 2018 for Application No. 2015114091, 53 pages.
Search Report dated Aug. 5, 2016 for Russian Application No. 2015114091, 2 pages.
Search Report dated Oct. 10, 2016 for Russian Application No. 201511409112, 2 pages.
Supplementary Search dated Mar. 6, 2017 for Chinese Application No. 201380054490.7, 1 page.
Wikipedia, "Retransmission (data networks)," Jun. 1, 2012, retrieved from https://en.wikipedia.org/w/index.php?title=Retransmission_(data_networks)&oldid=495485023, on Apr. 22, 2021, 2 pages.
Wikipedia "Transmission Control Protocol," Oct. 16, 2012, retrieved from https://en.wikipedia.org/w/index.php?title=Transmission_Control_Protocol&oldid=518129752, on Apr. 22, 2021, 22 pages.
Zhang J., et al., "Acoustic Communication in Wireless Sensor Networks," In: CS651, Wireless Sensor Networks D6, Dec. 2005, pp. 1-8.
Zheng et al., "Wireless Sensor Network Technology", Machinery Industry Press, Jun. 2012, p. 93 (77 pages).
International Preliminary Report on Patentability for Application No. PCT/EP2013/071070, dated Nov. 21, 2014, 6 pages.
International Preliminary Report on Patentability for Application No. PCT/EP2020/056222, dated Sep. 23, 2021, 14 pages.
International Preliminary Report on Patentability for Application No. PCT/EP2020/056227, dated Sep. 23, 2021, 11 pages.
International Preliminary Report on Patentability for Application No. PCT/GB2014/053017, dated Dec. 10, 2015, 19 pages.
International Preliminary Report on Patentability for Application No. PCT/GB2016/051729, dated Sep. 20, 2017, 11 pages.
International Preliminary Report on Patentability for Application No. PCT/GB2016/052829, dated Dec. 13, 2017, 21 pages.
International Preliminary Report on Patentability for Application No. PCT/GB2016/052831, dated Sep. 8, 2017, 8 pages.
International Preliminary Report on Patentability for Application No. PCT/GB2017/050781, dated Feb. 27, 2018, 13 pages.
International Preliminary Report on Patentability for International Application No. PCT/EP2013/071070, dated Jun. 19, 2015, 13 pages.
International Preliminary Report on Patentability for PCT/GB2014/053027 dated Dec. 10, 2015, 19 pages.
International Search Report and Written Opinion for Application No. PCT/EP2013/059954, dated Sep. 25, 2013, 8 pages.
International Search Report and Written Opinion for Application No. PCT/EP2020/056227, dated Aug. 31, 2020, 19 pages.
International Search Report and Written Opinion for Application No. PCT/GB2016/051729, dated Aug. 22, 2016, 20 pages.
International Search Report and Written Opinion for Application No. PCT/GB2016/052829, dated Mar. 7, 2017, 21 pages.
International Search Report and Written Opinion for Application No. PCT/GB2016/052831, dated Nov. 29, 2016, 13 pages.
International Search Report and Written Opinion for Application No. PCT/GB2016/052832, dated Nov. 24, 2016, 12 pages.
International Search Report and Written Opinion for Application No. PCT/GB2017/050781 dated Jun. 14, 2017.
International Search Report and Written Opinion for Application No. PCT/EP2020/056222, dated Sep. 29, 2020, 25 pages.
International Search Report and Written Opinion for Application No. PCT/EP2013/071070, dated Apr. 2, 2014, 6 pages.
International Search Report and Written Opinion for International Application No. PCT/EP2020/056235 dated May 29, 2020, 9 pages.
International Search Report and Written Opinion of the International Searching Authority for PCT/GB2014/053027, dated Apr. 22, 2015, 13 pages.
International Search Report for Application No. PCT/EP2013/071069, dated Dec. 20, 2013, 3 pages.
"ISO/IEC 13157-1: 2014—Information Technology—Telecommunications and Information Exchange between Systems—NFC Security Part 1 NFC-SEC NFCIP-1 Security Services and Protocol," Aug. 15, 2014, 2 pages.
ITU-T E.212 standard, The international identification plan for public networks and subscriptions, May 2008, 28 pages.
Japanese Office Action, Application No. 2018-033546, dated Oct. 29, 2019, 14 pages.
"Load Detecting Power Supply," National Semiconductor RD-1066 Production Applications Design Center, Dec. 2008, 17 pages.
Lu Y., et al., "Photonic Crystal Based All-Optical Pressure Sensor," 2011, pp. 621-623.
Mozek et al., "Digital Temperature Compensation of Capacitive Pressure Sensors" Informacije, vol. 40, 2010.
Notice of Allowance for Japanese Application No. 2015-512037, dated Dec. 15, 2015, 5 pages.
Notice of Issuance dated Jun. 16, 2021 for Chinese Application No. 201710348338, 12 pages.
Notice of Opposition for European Application No. 14784354.4, dated Feb. 20, 2020, 43 pages.
Notice of Opposition for European Application No. 14784354.4,dated Feb. 20, 2020, 69 pages.
Notice of Opposition dated Oct. 8, 2019 for European Application No. EP13779773.4, 7 pages.
Notice of Opposition dated Feb. 19, 2020 for European Application No. 13774188.0, 95 pages.
Notice of Reasons for Refusal for Japanese Application No. 2016520611, dated May 2, 2017,12 pages (with English translation).
Notice to File a Response dated Oct. 19, 2016 for Korean Application No. 10-2015-7010072, 12 pages.
Observations by third parties for European Patent No. 2908673 (13774188.0), mailed May 26, 2021, 13 pages.
Office Action and Search Report dated Sep. 29, 2019 for Chinese Application No. 201680038584.9, 17 pages.

(56) References Cited

OTHER PUBLICATIONS

Office Action dated Mar. 21, 2016, for Chinese Application No. 201380025370.4, 23 pages.
Office Action dated Nov. 17, 2017 for Chinese Application No. 201480055728.2, 8 pages (20 pages with translation).
Office Action for Canadian Application No. 2,872,764, dated Aug. 31, 2016, 6 pages.
Office Action for Canadian Application No. 2,872,764, dated Oct. 5, 2015, 6 pages.
Office Action for Canadian Application No. 2,886,922, dated Mar. 4, 2016, 3 pages.
Office Action for Canadian Application No. 2,922,280, dated Jan. 20, 2017, 4 pages.
Office Action for Canadian Application No. 2,997,062, dated Mar. 4, 2019, 6 pages.
Office Action for Chinese Application No. 201380025370.4, dated Oct. 11, 2016, 3 pages (8 pages with translation).
Office Action for Chinese Application No. 201380054442.8, dated Jun. 28, 2017, 8 pages (20 pages with translation).
Office Action For Chinese Application No. 2019103229551, dated Nov. 24, 2021, 16 pages.
Office Action for Japanese Application No. 2015-537196, dated Mar. 22, 2016, 3 Pages (7 pages with translation).
Office Action for Japanese Application No. 2015-537196, dated Nov. 22, 2016, 4 pages (9 pages with translation).
Akbar et al., "Temperature compensation of piezoresistive pressure sensors" Sensors and Actuators A, vol. 33, 1992, 8 pages.
Application and File History for U.S. Appl. No. 14/401,511, filed Nov. 14, 2014, Inventor: Christopher Lord, 561 pages.
Application and File History for U.S. Appl. No. 14/432,750, filed Mar. 31, 2015, Inventor: Christopher Lord.
Application and File History for U.S. Appl. No. 14/432,752, filed Mar. 31, 2015, Inventor: Christopher Lord, 387 pages.
Application and File History for U.S. Appl. No. 15/027,344, filed Apr. 5, 2016, 535 pages, Inventors: Lord et al.
Application and File History for U.S. Appl. No. 15/231,359, filed Aug. 8, 2016, Inventor: Christopher Lord, 572 pages.
Application and File History for U.S. Appl. No. 16/188,862, filed Nov. 13, 2018, 444 pages, Inventor: Lord et al.
Application and File History for U.S. Appl. No. 15/739,019, filed Dec. 21, 2017, Inventor, Dickens, 525 pages.
Application and Filing Receipt for U.S. Appl. No. 16/454,127, filed Jun. 27, 2019, Inventor: Christopher Lord, 641 pages.
Bluetooth, "Bluetooth Smart Technology: Powering the Internet of things," Retrieved from http://web.archive.org/web/20141110191357/http://www.bluetooth.com/Pages/Bluetooth-Smart.aspx, Nov. 10, 2014, 2 pages.
Boge et al., "Handbuch Elektrotechnik" Wiesbaden, Germany: Vieweg Verlag, 2004, Ed. 3 ISBN: 3-528-24944-7, 6 pages.
Cambridge dictionary online, "Dictionary definition for Tap", Jan. 27, 2020, 16 pages.
Communication by Great Britain Application No. 2497616, dated Aug. 4, 2013, 2 pages.
Decision of Grant dated Feb. 16, 2016 for Russian Application No. 2014150496, 7 pages.
Decision of Refusal dated May 10, 2022 for Japanese Application No. 2020-143411, 6 pages.
Decision to Grant for Japanese Application No. 2015-537196, dated Jul. 6, 2017, 3 pages (6 pages with translation).
Decision to Grant for Japanese Application No. 2018-515461, dated Aug. 6, 2019, 5 pages.
Decision to Grant dated Feb. 28, 2019 for Russian Application No. 2018129541, 14 pages.
Decision to Grant dated Oct. 30, 2018 for Russia Application No. 2017145807, 13 pages.
Decision to Grant dated Apr. 29, 2016 for Russian Application No. 122987, 12 pages.
Decision to Grant dated Aug. 24, 2016 for Russian Application No. 201511435112, 12 pages.

Dialog Semiconductor, "DA14580—Low Power Bluetooth Smart SoC," Retrieved from http://www.dialog-semiconductor.com/products/bluetooth-smart/smartbond-da-14580, © 2014, Jan. 29, 2015, Version. 3.1, 158 pages.
European Patent Office Communication for Application No. EP16729349.7, dated Feb. 12, 2020, 53 pages.
Examination Report dated Feb. 3, 2020 for European Application No. 18207065.6, 5 pages.
Examination Report dated Sep. 13, 2018 for New Zealand Application No. 740653, 4 pages.
Examination Report No. 1 dated May 2, 2016 for New Zealand Application No. 717778, 4 pages.
Extended European Search Report for Application No. 18207065, dated Apr. 12, 2019, 8 pages.
Extended European Search Report for Application No. 19164915.1, dated Jul. 8, 2019, 8 pages.
Extended Report for European Application No. 13779773.4, dated Jun. 20, 2016, 2 pages.
Extended Report dated Aug. 15, 2016 for New Zealand Application No. 71778, 3 pages.
Extended Report dated Nov. 16, 2016 for New Zealand Application No. 717778, 1 page.
Extended Search Report dated Jun. 24, 2019 for European Application No. 19164911.0, 8 pages.
Extented European Search Report for European Application No. 18159788, dated Jul. 9, 2018, 8 pgs.
Farsalinos Konstantinos et al., "Evaluation of Electronic Cigarette Use (Vaping)Topography and Estimation of Liquid Consumption: Implications for Research Protocol Standards Definition and for Public Health Authorities Regulation" Int J Environ. Res. Public Health, 2013, pp. 2500-2514.
First Examination Report for Australian Application No. 2013261801, dated Jul. 10, 2015, 2 pages.
First Extended Report for Australian Application No. 2013331849, dated Dec. 1, 2015, 3 pages.
First Extended Report for Australian Application No. 2014333571, dated Nov. 25, 2016, 4 pages.
First Office Action and Search Report for Chinese Patent Application No. 201811568130, dated Apr. 8, 2021, 22 pages.
First Office Action for Chinese Application No. 201380054442.8 dated Aug. 30, 2016, 4 pages.
Freescale semiconductor, 100 kPa on-chip temperature compensated and calibrated silicon pressure sensors, 10 pages.
Freescale semiconductor, integrated silicon pressure sensor on-chip signal conditioned, temperature compensated and calibrated, 18 pages.
Freescale Semiconductor, "Miniature I2C Digital Barometer," Pressure, MPL115A2, Retrieved from the Internet: URL: https://strawberry-linux.com/pub/MPL115A2.pdf, on Oct. 19, 2011, 8 pages.
Freescale semiconductor, temperature compensation methods for the Motorola X-ducer pressure sensor element, 11 pages.
Grounds of Appeal for European Patent No. 2908673 (13774188.0), mailed on Feb. 23, 2022, 36 pages.
IEEE, 802.15.1 (Jun. 14, 2002) IEEE Standard for Telecommunications and Information Exchange Between Systems—LAN/MAN—Specific Requirements Part 15: Wireless Medium Access Control (MAC) and Physical Layer (PHY) Specifications for Wireless Personal Area Networks (WPANs), 2 pages.
IEEE, IEEE Publishes the 802.11v Amendment Titled Wireless Network Management to Extend the Base IEEE 802.11.TM. Wireless LAN Standards (May 13, 2011), 1 page.
IEEE Standards Association, "P802.11ah—IEEE Draft Standard for Information Technology—Telecommunications and Information Exchange Between Systems—Local and Metropolitan Area networks—Specific Requirements—Part 11: Wireless LAN Medium Access Control (MAC) and Physical Layer," 2016, 1 page.
International Preliminary Report on Patentability for Application No. Application No. PCT/GB2016/052832, dated Sep. 20, 2017, 15 pages.
International Preliminary Report on Patentability for Application No. PCT/EP2013/059954, dated Jul. 10, 2014, 6 pages.
International Preliminary Report on Patentability for Application No. PCT/EP2013/071069, dated Apr. 28, 2015, 13 pages.

(56) References Cited

OTHER PUBLICATIONS

Written Opinion for Application No. PCT/GB2016/052829, dated Sep. 29, 2017, 8 pages.
Youtube., "A PBusardo Review—The Provari V2—Provape," published on Feb. 28, 2012, https://www.youtube.com/watch?v=FG9DQbowrDA, 1 page.
Youtube., "Tips Tutorial for Using Your ProVape Electronic Cigarette", Vlogger Phil Busardo, published on Jun. 30, 2012, 5 pages.
Office Action for Japanese Application No. 2017-153826, dated Jun. 19, 2018, 3 pages (6 pages with translation).
Office Action for Japanese Application No. 2018-033546, dated Feb. 15, 2019, 5 pages (12 pages with translation).
Office Action for Japanese Application No. 2018-086172, dated Dec. 8, 2020, 5 pages.
Office Action dated Feb. 3, 2020 for Japanese Application No. 2018-086172, 17 pages.
Office Action dated Aug. 11, 2020 for Japanese Application No. 2019112583, 6 pages.
Office Action dated Mar. 14, 2022 for Russian Application No. 2021126453, 19 pages.
Office Action dated Mar. 15, 2016 for Japanese Patent Application No. 2015-537195, 2 pages.
Office Action dated Jun. 17, 2020 for Russian Application No. RU201603517, 10 pages.
Office Action dated Oct. 17, 2016 for Korean Application No. 10-2015-7010071, 13 pages.
Office Action dated Oct. 17, 2019 for Korean Application No. 10-2018-7038106, 17 pages.
Office Action dated Jul. 24, 2019 for Korean Application No. 10-2018-7035809, 22 pages.
Office Action dated Oct. 24, 2019 for Japanese Application No. 2018-033546,14 pages.
Office Action dated Sep. 26, 2016 for Chinese Application No. 201380054420.1 , 8 pages.
Office Action dated May 9, 2017 for Japanese Application No. 2016-520611, 13 pages.
Office Action dated Apr. 27, 2018 for Korean Application No. 20157010072,10 pages (19 pages with translation).
Office Action dated Apr. 27, 2018 for Korean Application No. 2018-028946712, 19 pages.
Office Action dated Aug. 11, 2016 for Korean Application No. 10-2014-7035205, 11 pages.
Office Action mailed dated Aug. 7, 2017 for European Application No. 13779773, 2 pages.
Office Action dated Dec. 28, 2018 for Korean Application No. 10-2018-7014831, 8 pages (15 pages with translation).
Office Action dated Jul. 26, 2017, for Korean Application No. 10-2016-7009422,9 pages (with translation 17 pages).
Office Action dated Mar. 24, 2021 for Chinese Application No. 201910322955.1, 16 pages.
Office Action dated Sep. 23, 2016, for Korean Application No. 10-2014-7035201, 12 pages.
Ortman T., "ProVari Menu Tour," published on Mar. 10, 2011, Youtube, as available at https://www.youtube.com/watch?v=IPKQOgQ42z8, Feb. 18, 2020, 18 pages (with machine-generated transcript).
Provape., "Screen Capture of ProVari Variable Voltage Information Page," as it appeared on May 8, 2012, via a query on web.archive.org, 10 pages.
Provape., "ProVari Menu Tour", Youtube, published on Mar. 10, 2011, 18 pages.
Provape., "ProVari Owner's Manual," 2010, available on https://provape.com/, Dec. 16, 2011, 16 pages.
Sadaphal et al., "Random and Preiodic Sleep Schedules for Target Detection in Sensor Networks", Tata Research Development and Design Centre and Department of Computer Science and Engineering—Indlan institute of Technology, Mar. 17, 2008, 12 pages.
Search Report for Chinese Application No. 201910151850.4 dated Apr. 28, 2021, 2 pages.
Search Report For Chinese Application No. 2019103229551, dated Mar. 13, 2021, 3 pages.
Search Report dated Aug. 23, 2017 for Japanese Application No. 2016-227701, 26 pages (40 pages with translation).
Search Report dated Jul. 26, 2016, and Decision to Grant dated Aug. 24, 2016, for Russian Application No. 2015114090, 14 pages.
Search Report dated Nov. 30, 2015 for Great Britain Application No. GB1511566.0, 4 pages.
Search Report dated Feb. 10, 2016 for Great Britain Application No. GB1517089.7, 5 pages.
Search Report dated Feb. 22, 2016 for Great Britain Application No. GB1517092.1, 3 pages.
Search Report dated Feb. 23, 2016 for Great Britain Application No. GB1517094.7, 4 pages.
Search Report dated Mar. 27, 2018 for Russian Application No. 2016147728, 3 pages (6 pages with translation).
Search Report dated Mar. 28, 2017 for Japanese Application No. 2016-520611,18 pages (with translation 46 pages).
Second Examination Report for Australian Application No. 2013261801, dated Jun. 23, 2016, 3 pages.
Second Extended Report for Australian Application No. 2013331849, dated Feb. 5, 2016, 3 pages.
Second Extended Report for Australian Application No. 2014333571, dated Jan. 23, 2017, 4 pages.
Second Office Action and Supplemental Search dated Jun. 19, 2017 for Chinese Application No. 201380054420.1.
Second Office Action for Chinese Application No. 201710348338.X, dated Mar. 25, 2020, 17 pages.
Silicon Microstructures, Active Temperature Compensation and Calibration for MEMS pressure sensors with constant voltage, 6 pages.
Stiny et al., "Grundwissen Elektrotechnik und Elektronik," Haag a. d. Am per, Germany: SpringerVieweg, 2018, Ed. 7 ISBN: 978-3-658-18318-9, 3 pages.
Third Extended Report for Australian Application No. 2014333571, dated May 23, 2017, 4 pages.
Transactions of the Royal Society of Edinburgh, 1848, vol. XVIII, containing the Makerstoun Magnetical and Meteorological Observations for 1844, Robert Grant Sons, pp. 419-424.
Vaishali et al., "Random and Periodic Sleep Schedules for Target Detection in Sensor Networks", Journal of Computer Science and Technology, May 2008, vol. 23(3), pp. 343-354.
Wikipedia, "Electronic Cigarette," Retrieved from the Internet: URL: https://en.wikipedia.org/wZindex.php?title=Electronic_cigarette, version of Sep. 18, 2012, 17 pages.
Williams, Monique et al., "Variability Among Electronic Cigarettes in the Pressure Drop, Airflow Rate, and Aerosol Production" Nicotine Tobacco Research Advance Access, Oct. 12, 2011, 8 pages.
Written Opinion for Application No. PCT/EP2013/059954, dated Apr. 16, 2014, 5 pages.

* cited by examiner

ELECTRONIC INHALATION DEVICE

RELATED APPLICATION

This application is a continuation of application Ser. No. 16/454,127, filed Jun. 27, 2019, which is a continuation of application Ser. No. 14/432,750 filed Mar. 31, 2015, now U.S. Pat. No. 10,375,990, issued Aug. 13, 2019, which in turn is a National Phase entry of PCT Application No. PCT/EP2013/071072, filed Oct. 9, 2013, which in turn claims priority to and benefit of United Kingdom Patent Application No. GB1218820.7, filed Oct. 19, 2012, each of which is hereby fully incorporated herein by reference.

TECHNICAL FIELD

The present disclosure relates to electronic inhalation devices. More particularly, but not exclusively, the present disclosure concerns electronic cigarettes comprising a computer and a transmitter.

BACKGROUND

Electronic inhalation devices are typically cigarette-sized and function by allowing a user to inhale a nicotine vapor from a liquid store by applying a suction force to a mouthpiece. Some electronic inhalation devices have a pressure sensor that activates when a user applies the suction force and causes a heater coil to heat up and vaporize the liquid. Electronic inhalation devices include electronic cigarettes.

SUMMARY

An electronic inhalation device comprising a mouthpiece and a control unit, the control unit comprising a power cell and a computer, where the computer comprises a computer processor, a memory and an input-output means; wherein the device further comprises a transmitter connected to the computer and the computer is configured in use to collect and store use data relating to a user's use of the device in the computer memory and transmit the use data.

Storing data has the advantage that data relating to a user's intake and usage habits can be monitored. This is important when the device is used as a replacement for cigarettes since it enables the replacement therapy to be monitored and a determination made as to whether it is working. By transmitting the stored use data, the user is able to transmit the data to a receiving device in order to interpret it and monitor their use of the device.

Suitably, the electronic inhalation device is an electronic cigarette.

Suitably, the computer is a microcontroller.

Suitably, the transmitter is configured to transmit the use data by wireless means.

Suitably, the transmitter is an audio signaling means and is configured to transmit the use data by sound.

Providing a wireless transmission means enables the data to be transmitted and shared without the cumbersome use of a cable interface. This eliminates the need for an access port on the device. Transmitting by wireless means requires a transmitting device within the device. When the transmission is made by sound, the transmitter can be a simple component such as a buzzer or speaker. This is a low cost item yet effective component and allows transmission of data through modulated sound. The sounder can also serve other functions.

Suitably, the use data comprises an inhalation count, where the inhalation count is a count of the number of inhalations a user has taken on the device. Suitably, the inhalation count is stored in 1 byte or 2 bytes of data memory.

Suitably, the use data comprises an average inhalation time, where the average inhalation time is the mean average of the inhalations counted in the inhalation count. Suitably, the average inhalation time is stored in 1 byte or 2 bytes of data memory.

Suitably, the use data comprises a session count, where the session count is a count of the number of inhalation sessions. Suitably, the session count is stored in 1 byte or 2 bytes of data memory. Suitably, an inhalation session ends when the device is inactive for a predetermined inactivity time following inhalation on the device.

By storing data relating to number of inhalations, average inhalation time, and number of sessions, the data storage requirements are minimized yet the important information is still stored. The number of inhalations and number of sessions is just a count and this value can be changed and updated in the computer memory so that only a single value is required. Likewise, the average duration can be changed and updated in the memory so that only a single value is required. Thus the memory space requirements are greatly minimized.

Suitably, the use data is stored in 8 bytes or less of data memory.

Suitably, the use data is optimized for transmission by sound.

Minimizing the data has the advantage that the data can be transmitted more quickly and even repeated transmissions can be made in a short duration so that the user is not waiting for transmissions to be made. Having stored data in 8 bytes or less of data memory provides minimal data for transmission thus speeding up the transmission process. Minimal data may be important when the data is being transmitted by modulated sound.

Suitably, the use data further comprises header data at the start of the data to indicate the start of the data.

Suitably, the use data further comprises footer data that the end of the data to indicate the end of the data.

Suitably, the use data further comprises configuration data towards the start of the data to indicate how the data is configured for transmission.

Suitably, the configuration data indicates the frequency range of the data transmission.

Suitably, the configuration data indicates the duration of the data transmission.

Suitably, the configuration data indicates the intensity of the data transmission.

The extra data provided with the core use data serves to provide useful information to the receiving means about the data being transmitted. Having header data that the receiving means is waiting for ensures that the receiving means knows that data will follow this header data. Likewise, having footer data ensures that the receiving means knows that the data transmission is over. The configuration data is important since it enables the receiver to configure itself and prepare for data being sent. When transmission is by sound, data can be modulated in different frequency ranges, over different time period and will different intensities, so it is an advantage to know how the data will be sent.

Suitably, the use data comprises details of individual inhalation events. Suitably, details of individual inhalation events include the date and time of each inhalation. Suitably, details of individual inhalation events include the duration of each inhalation Suitably, the computer is configured to transmit a first transmission version of the use data and a second transmission version of the use data successively.

Suitably, the first transmission version is substantially the same as the second transmission version.

Suitably, the first transmission version and the second transmission version each has a different frequency range.

Suitably, the first transmission version and the second transmission version each has a different duration.

Suitably, the first transmission version and the second transmission version each has different signal intensity.

Suitably, the computer is configured in use to transmit three or more transmission versions of the use data successively.

Suitably, the computer is configured in use to transmit the use data repeatedly.

By transmitting the data more than once, the receiver is more likely to receive a complete message. If there is interference during one transmission, other transmissions may get through without interference. By varying parameters such as frequency ranges, durations and intensities, the data that is affected under one set of conditions may not be affected under another. Thus, there is a higher chance that the receiver will receive the data. Also, by transmitting the data more that once, the receiver is able to verify the data that is sent.

Suitably, the computer is configured in use to transmit the use data at a frequency substantially above the frequency range of typical background noise.

Suitably, the computer is configured in use to transmit the use data at a frequency substantially above the human hearing frequency range.

There are typical background noises in normal living and working environments. By providing a signal substantially outside of these background noises gives a higher chance that the transmitted signal will be received by the receiver. Also, where the data is transmitted by modulated sound, the transmission noise may be undesirable so providing transmission at a frequency about the human hearing frequency range prevents this.

Suitably, the computer is configured to clear the use data from the memory after transmission.

Suitably, the computer is configured to clear the use data from the memory when controlled to do so by the user.

Once the data has been transmitted, clearing the data from the memory allows future data to be stored.

Suitably, the electronic inhalation device further comprises a pressure sensor connected to the computer.

Suitably, the computer is configured in use to transmit the use data when the pressure sensor detects operation of the device outside of normal use.

Suitably, the computer is configured in use to transmit the use data when the pressure sensor detects blowing into the device.

Suitably, the computer is configured in use to transmit the use data when the pressure sensor detects sucking on the device.

Suitably, the computer is configured in use to transmit the use data the pressure sensor detects a short burst of blowing into the device.

Suitably, the computer is configured in use to transmit the use data when the pressure sensor detects a short burst of sucking on the device.

Suitably, the computer is configured in use to transmit the use data when the pressure sensor detects two or more short bursts of blowing into the device.

Suitably, the computer is configured in use to transmit the use data when the pressure sensor detects two or more short bursts of sucking on the device.

Suitably, the computer further comprises a menu mode configured whereby the pressure sensor is used to activate the menu mode and select a menu option that starts transmission of the use data.

Using the pressure sensor to control the transmission of the data is advantageous since the pressure sensor may already be a feature of the product. Thus, additional components to control the transmission will not be needed. The control is also an internal control so there is less change of it being damaged.

Suitably, the computer is configured to clear the use data from the memory when a user selects a clear memory menu option.

Suitably, the computer is configured to clear the use data from the memory when the menu mode is exited.

Suitably, the computer is configured in use to notify the user by sound when the device has entered the menu mode.

Suitably, the computer is configured in use to notify the user by sound prior to transmission of the use data.

Suitably, the computer is configured in use to notify the user by sound when the transmission of the use data is underway.

Suitably, the computer is configured in use to notify the user by sound when the transmission of the use data is complete.

Suitably, the computer is configured in use to notify the user by sound when the transmission of the use data has been successfully received.

Suitably, the computer is configured in use to notify the user by sound when the transmission of the use data has not been successfully received.

Suitably, the computer is configured in use to notify the user by sound when the use data has been cleared from the computer memory.

Using sound to notify the user has the advantage that a number of different sound signals can easily be used that a user is able to distinguish between. Thus a user can easily identify where transmission has started, ended, succeeded or failed and the user can take action accordingly. This is especially an advantage when the device is controlled using a pressure sensor since the device will be in a user's mouth and a user will find it difficult to look at it. However, when the device is in the mouth, it will be near the user's ears so the sound will be easily heard.

Suitably, the device further comprises a microphone connected to the computer.

Suitably, the computer is configured to determine the background noise using the microphone and transmit the use data so as to substantially avoid the background noise.

Suitably, the computer is configured to start transmission when a start signal is received by the microphone.

Suitably, the computer is configured to end transmission when an end signal is received by the microphone.

Suitably, the computer is configured to retransmit the use data when a fail signal is received by the microphone.

Suitably, the computer is configured to clear the use data from the memory when a clear signal is received by the microphone.

Having a microphone is advantageous since it allows feedback to be received from the receiver and allows control of the transmission by the receiver. Also, a reading can be made of the background noise in order to process the transmission method to provide a transmission that is still able to be received.

Suitably, the electronic inhalation device comprises a mouthpiece end and a tip end, and the transmitter is located at the tip end.

Suitably, the transmitter is configured such that in use the use data is transmitted out of the tip end.

Suitably, the device comprises a longitudinal central axis and the transmitter is configured such that in use the use data is transmitted substantially parallel to the longitudinal axis and out from the tip end.

By setting up the transmission in relation to the physical dimensions of the device, the user is able to orientate the device relative to the receiver in order to optimize the transmission.

Suitably, the transmitter is a speaker.

As used herein the term electronic smoking device includes not only an electronic cigarette but also electronic smoking articles other than an electronic cigarette, for example a heat-not-burn (HNB) device or an electrically powered spray device in which a pressurized liquid is stored in a canister and released under the control of an electronic valve in response to a pressure drop produced by the user drawing on the device. These devices are referred to herein collectively as "electronic smoking devices", which term is intended to cover any electronic device which can be used as a substitute for a cigarette or as a cessation device, which does not involve the conventional combustion of tobacco.

BRIEF DESCRIPTION OF THE DRAWINGS

Embodiments will now be described, by way of example only, with reference to the accompanying drawings in which.

DETAILED DESCRIPTION

Figure 1:
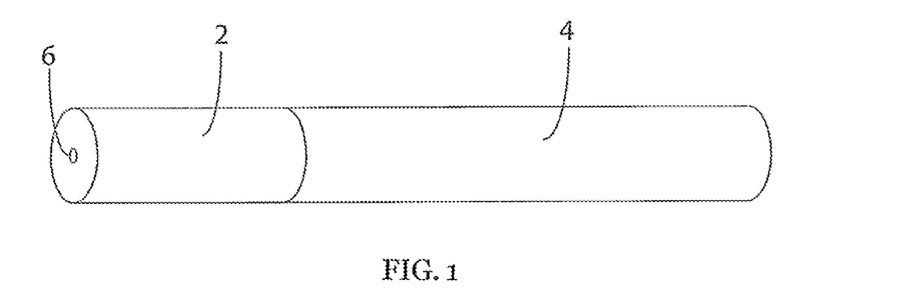
FIG. 1 is a side perspective view of an electronic inhalation device.
Figure 2:
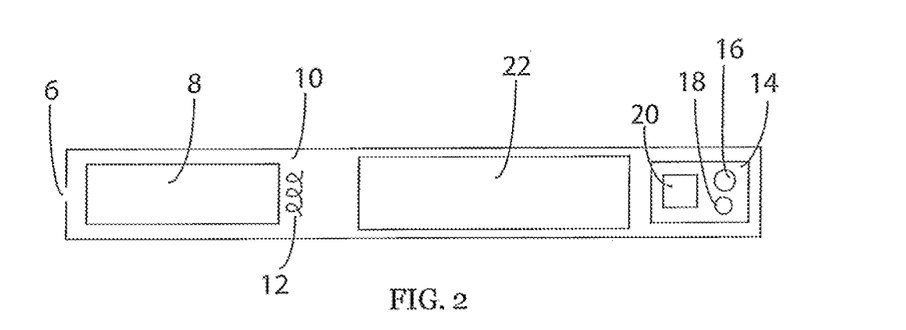
FIG. 2 is a side sectional view through the device of FIG. 1.

Referring to FIG. 1 and FIG. 2 there is shown an electronic inhalation device in the form of a cigarette-shaped electronic cigarette. The electronic cigarette has a mouthpiece 2 and a cigarette body 4. The mouthpiece 2 has an air outlet 6 at a first end and is connected to the cigarette body 4 at a second end.

Inside the electronic cigarette there is a liquid store 8 towards the mouthpiece end and a vaporizer 10 having a heating coil 12. The vaporizer 10 is arranged next to the liquid store 8 to allow liquid to be transferred onto the vaporizer 10 for vaporizing. A circuit board 14 contains a pressure sensor 16, a transmitter 18, and a computer 20. A power cell 22 provides power to the device. The power cell 22 and circuit board 14 with pressure sensor 16, transmitter 18 and computer 20 are contained in a control unit 24.

The general operation of the electronic cigarette is similar to that of known devices. When a user takes a draw on the electronic cigarette, a suction force is applied to the mouthpiece 2 and the air outlet 6. A reduced pressure inside the electronic cigarette causes the power cell 22 to provide power to the vaporizer 10 which in turn vaporizes the nicotine liquid solution. The resultant vapor is then inhaled by the user.

In this example the operation of the electronic cigarette goes beyond that of a general device. In a normal operating mode, when a user applies a suction force to the electronic cigarette, the resultant airflow causes a drop in pressure from ambient pressure to a lower pressure, within the device. The pressure sensor 16 provides a signal to the computer 20. The computer 20 runs software that monitors the pressure signal from the pressure sensor 16 and when it determines that the pressure has been reduced below a threshold pressure, the computer 20 provides an electrical current to the heating coil 12 in order to heat the heating coil 12 and vaporize liquid from the liquid store 8.

The software running on the computer 20 controls the operation of the device. The computer 20 also allows stores data on usage in a memory and allows transmission of this use data.

When a user uses the device in the normal mode of operation to inhale vaporized liquid such as nicotine vapor, the computer 20 monitors this usage. There are three parameters stored by the computer 20. These are the number of inhalations, the average time for an inhalation and the number of sessions.

The number of inhalations is simply a count of the number of times the device is activated to vaporize the liquid solution during normal use. This count starts at zero and is incremented each time the device is activated to deliver vapor during an inhalation. Thus, the count is incremented each time the pressure within the device is reduced below a threshold pressure thereby activating the vaporizer 10. Since this is just a count, the computer 20 stores the number of inhalations value and updates this accordingly. Thus, only a single value is stored in the computer memory.

By definition, 1 byte of data is equal to 8 bits of data. This enables a value between 0 and 255 to be stored in a single byte. In addition, 2 bytes of data enables a value between 0 and 65535 to be stored in two bytes. Thus, the number of inhalations value can easily be stored in 2 bytes of data and possibly 1 byte of data depending on usage.

When a user inhales on the inhalation device and the device activates to heat the heating coil 12 and vaporize the liquid in the liquid store 8, the device is only active while the user is applying a suction force. In fact, the computer 20 determines when the pressure measured by the pressure sensor 16 is reduced below a first threshold pressure value in order to activate the vaporizer 10. When the user ceases inhaling, the pressure within the device increases. The computer 20 determines when the pressure measured by the pressure sensor 16 increases above a second threshold pressure value and deactivates the vaporizer 10, stopping the electrical current flow to the vaporizer 10. The first threshold pressure value and second threshold pressure value are such that the drop in pressure has to be more to activate the device and less to deactivate the device. Thus the first threshold pressure value is a lower absolute pressure than the second threshold pressure value. The pressure change between the first threshold pressure and ambient pressure is greater than the pressure change between the second threshold pressure and ambient pressure. This helps to ensure that the device is not activated accidentally.

The time during which the computer 20 is supplying electrical current to the heating element 12 is an inhalation time. Thus, each inhalation time is dependent on the duration that the user inhales on the device. The computer 20 is able to calculate and store the average inhalation time, being the mean average.

After the first inhalation, the number of inhalations is 1 and the average inhalation time is just the first inhalation time. After the second inhalation, the number of inhalations is 2 and the average inhalation time is the sum of the first and second inhalation times divided by 2. After the nth inhalation, the number of inhalations is n and the average inhalation time is the sum of all inhalations from 1 to n, then divided by n.

The computer 20 is able to update the average inhalation time on each occasion such that it only has to store a single value. In 1 byte of data, the computer 20 can store values between 0 and 25.5 seconds in tenth of a second increments. Since an inhalation typically lasts between 2 and 3 seconds, the average inhalation time can easily be stored in 1 byte of data.

The electronic cigarette replicates the smoking of a real cigarette. A user will typically self-regulate their nicotine intake so whilst the total liquid in the liquid store 8 might provide significantly more nicotine than found in a single cigarette, a user will not inhale all of this at once. A user may use the device in sessions such that a user inhales a number of times in succession but then leaves a bigger time gap than between inhalations before starting again.

When a user inhales on the device, the computer 20 is able to determine the time that has elapsed since the previous inhalation. The computer then determines whether this time is greater than a threshold time period that defines a new smoking session. So if the wait between an inhalation and a subsequent inhalation is greater than a predetermined new session time, the computer identifies the subsequent inhalation as the start of a new session.

The computer 20 is able to count the number of sessions and then update this number as a single value. In 1 byte of data, the computer 20 can store numbers between 0 and 255. In 2 bytes of data, the computer 20 can store numbers between 0 and 65535. Thus the number of sessions can be stored in 1 byte or 2 bytes of data.

As the computer 20 stores use data values, these are updated so that the values are always current following an inhalation. At some point a user may decide to access this information.

A transmitter 18 is connected to the computer 20 and a user can transmit the use data using the transmitter 18. In order to begin transmission, a user must first activate the transmitter 18. There are a number of possibilities for activating the transmission of the data, an example activation makes use of the pressure sensor 16.

The pressure sensor 16 is used in normal operation to inhale a vaporized liquid. So when a user makes use of the pressure sensor in a way not normally used by the pressure sensor, the device can be used to transmit the use data.

When a user has finished using the device and wishes to transmit the use data they can do this by carrying out an action on the device that is different to how they use it in a normal mode. In a normal mode, a user typically inhales on the device for 2 to 3 seconds, replicating the action of smoking a real cigarette. In this situation the computer 20 receives a signal from the pressure sensor 16 and activates the vaporizer 10, heating up the heating coil 12.

To begin transmitting, a user can blow briefly into the device. The pressure sensor 16 sends a signal to the computer 20, and the computer recognizes that this is not normal operation but a signal to begin transmitting. Alternatively a user can blow briefly into the device, suck suddenly on the device in a quick burst or indeed blow or suck two or more times in rapid succession. In each of these circumstances, the pressure sensor 16 will send a signal to the computer 20 and the computer 20 will determine that this is not normal operation but a signal for the device to begin transmitting. When the device leaves normal mode and enters into transmission state, the vaporizer 10 is prevented from activating so that the user can further control the device using the pressure sensor 16 without activating the heating element 12.

The transmitter 18 may be a wireless transmitter therefore transmitting the use data by wireless means to a corresponding receiver. In this example, the transmitter 18 is a sounder such as a buzzer or speaker and transmits the data using sound. The computer 20 interprets the data and causes the transmission of the use data by sound.

Since transmission is generally directional, the transmitter 18 can be oriented and fixed in place relative to the outer cigarette body 4 such that a user is able to determine the transmission direction by looking at the device. In this example, the direction of transmission is out from the tip of the electronic cigarette in a direction parallel to the electronic cigarette.

Thus a user knows that pointing the electronic cigarette at a receiver will give the maximum transmission.

When the transmission is made by sound, a corresponding receiver uses a microphone. In this example, the receiving device is a smart phone having a built in microphone. The smart phone comprises a computer and a software application can be loaded onto the smart phone in order to configure the smart phone to be a receiver for the electronic cigarette transmission.

In use, the electronic cigarette transmits the use data as a sound signal and this sound signal can be detected and recorded on the smart phone. The computer on the smart phone can then extract the data and present this visually to the user.

Since the use data is being transmitted by sound and relies on sound being recorded by the receiving device, any background noise, as is common in most daytime environments, may interfere with the signal and prevent the receiving device from receiving the signal. In order to combat this, the sound signal is broadcast in a frequency range that is outside of most background noise frequency ranges. In another example, because the modulated sound signal may not be a desirable sound for the user, the sound signal could be transmitted at a frequency outside the frequency of human hearing. Thus a user would not heat the sound signal.

In order for the user to identify when a device is ready to transmit, is transmitting and has finished transmitting data, a sound signal corresponding to each of these events is communicated to the user. For example, a single beep may mean ready, a double beep may mean transmitting, and three beeps may mean finished.

Since the use data is only stored in a few bytes of data, this data can easily and quickly be transmitted by modulated sound. There is also the possibility that the data can be transmitted more than once during a transmission session. For example, when a user initiates transmission of the use data, a first version may be transmitted followed directly by a second version, prior to the transmission ending. Any receiving device would be configured to know the number of times that a signal was being transmitted. Having two versions enables two different sound signals to be used to transmit the same data. For example, the second version sound signal could be transmitted at a different frequency, have a different duration, or have a different intensity. This would provide a way to avoid background noise and ensure that the signal and data is received by the receiving device.

In another example, this idea can be taken further and three of more successive version of the data may be transmitted with different sound signals so as to maximise the probability that the receiver receives the signal. In another example, the use data may be transmitted repeatedly until the user stops the signal. This enables the user to position the receiver and wait until the receiving device has successfully received the data.

When a user has finished with the transmission of the data they will want to clear the data from the computer memory so that new data can be stored in the device memory. A user may do this using the pressure sensor 16. Alternatively the computer 20 may assume that the data has been transmitted and automatically clear the memory. A user is notified by a sound signal when the data has been cleared from the computer memory, such as 4 beeps.

In order to help the receiver identify the start and end of the sound signal transmission, header data representing the start of the signal and footer data representing the end of the signal can be added to the use data. Thus, the receiver is able to identify the start of the signal and end of the signal. This is particularly useful when the use data is transmitted more than once.

Figure 3:
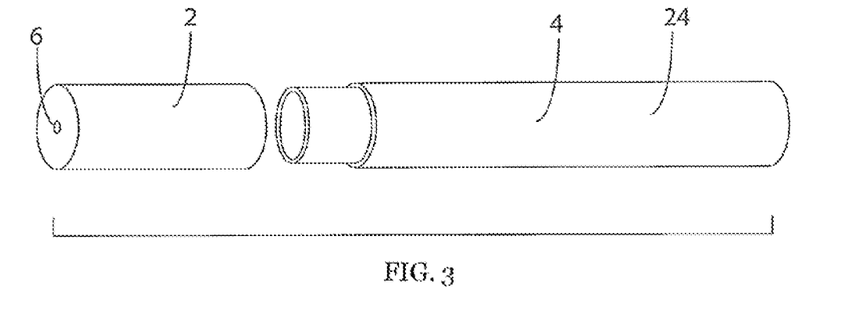
FIG. 3 is an exploded side perspective view of an electronic inhalation device having separated mouthpiece and control unit.
Figure 4:
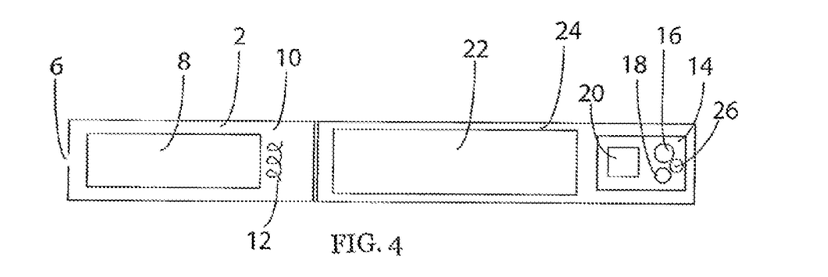
FIG. 4 is a side sectional view through the device of FIG. 3 with connected mouthpiece and control unit.

FIG. 3 and FIG. 4 show a device similar to that shown in relation to FIG. 1 and FIG. 2. The difference is that the mouthpiece 2 is releasably-attachable to the cigarette body 4. The mouthpiece comprises a female screw thread connection means, the cigarette body is a control unit 24 having a male screw thread connection means. The mouthpiece 2 and the control unit 24 can be screwed together or taken apart.

In this example, the mouthpiece 2 comprises the liquid store 8 and the vaporizer 10 with heating coil 12. The control unit 24 comprises the power cell 22 and circuit board 14 with pressure sensor 16, transmitter 18 and computer 20. The screw thread connection provides an electrical connection such that when the mouthpiece 2 and control unit 24 are screwed together, electrical current can be delivered to the heating coil 12 upon activation of the vaporizer 10.

Another difference is that the control unit 24 further comprises a microphone 26. The microphone 26 enables the device to act as both a transmitter and a receiver. In use, the computer 20 is able to measure the background noise using the microphone 26. So rather than providing a use data sound signal that avoids a typical background noise, the computer 20 can configure the sound signal so that it avoids the measured background noise.

The computer 20 is then able to transmit this modified sound signal and there is a higher probability that the receiver will successfully receive the signal. Since the computer 20 is using a measured background noise it may be useful to add configuration data towards the start of the use data sound signal. This configuration data gives information about the signal frequency, duration and intensity to allow the receiver to adjust accordingly in order to receive the transmission.

The microphone 26 also provides a means by which the device can be activated for transmission of the use data. For example, a user could use the receiving device to send out a start sound signal. This would be picked up by the microphone 26 and cause the transmission of the use data to begin. Where the transmission is ongoing, the receiving device could send out a sound signal to end transmission. If the receiving device has not successfully received the use data, it could send out a sound signal to repeat transmission of the use data. If the receiving device has successfully received transmission of the use data is could send out a signal to enable to device to enter normal mode and clear the use data from the memory. When the computer 20 identifies that the use data has been transmitted successfully it notifies the user of this by sound. Likewise, when the computer 20 identifies that the use data has not been transmitted successfully it notifies the user of this by sound.

The computer 20 is able to leave the transmitting mode when the vaporizer 10 is unscrewed from the control unit 24.

Figure 5:
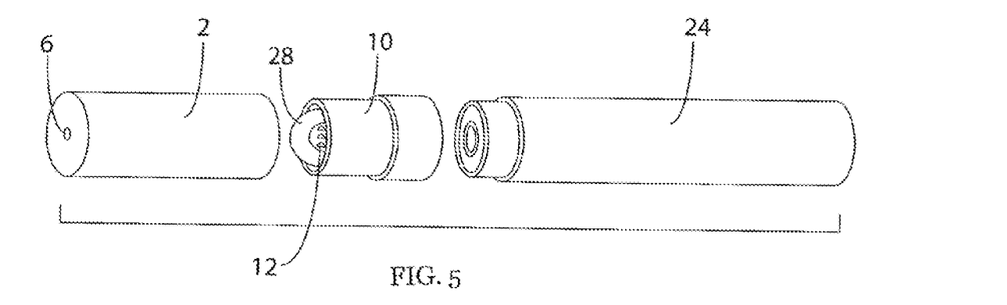
FIG. 5 is an exploded side perspective view of an electronic inhalation device having separated mouthpiece, vaporizer and control unit.
Figure 6:
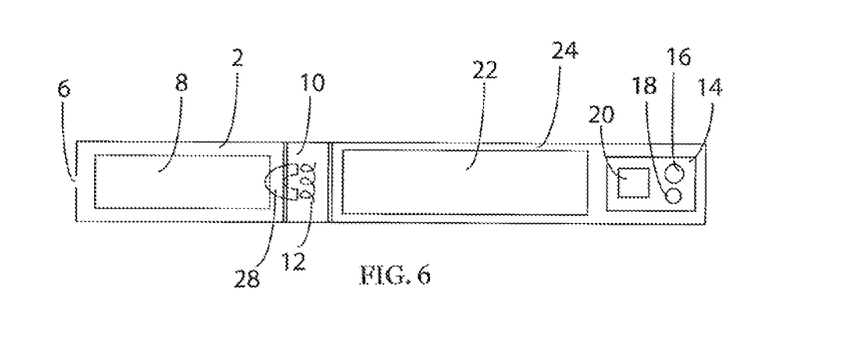
FIG. 6 is a side sectional view through the device of FIG. 5 with connected mouthpiece, vaporizer and control unit.

FIG. 5 and FIG. 6 show a device similar to that shown in relation to FIG. 3 and FIG. 4. However in this example, the vaporizer 10 is removable from the mouthpiece 2. Also, as with the device of FIG. 1 and FIG. 2, there is no microphone on the circuit board 14.

The mouthpiece 2 has a cylindrical opening that forms an interference push-fit with the vaporizer 10. As such the mouthpiece 2 can be separated from the vaporizer 10. The mouthpiece 2 comprises the liquid store 8. The vaporizer 10 comprises the heating coil 12 and a wick 28. The wick 28 protrudes from the end of the vaporizer 10 such that when the mouthpiece 2 and the vaporizer 10 are connected, the wick 28 dips into the liquid store 8.

In use, as a user inhales on the device, liquid is transferred from the liquid store 8 and onto the wick 28 before being transferred onto the heating coil 12 for vaporization.

Figure 7:
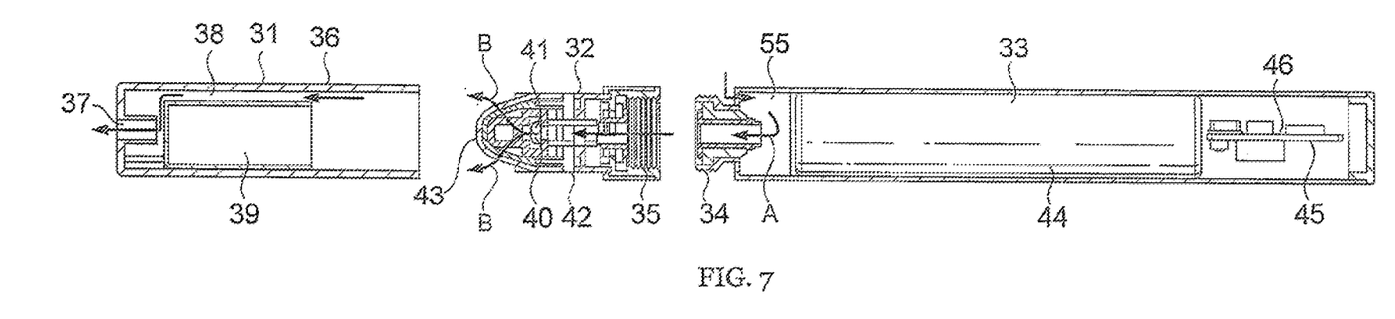
FIG. 7 is an exploded longitudinal sectional view of another embodiment of an electronic inhalation device similar to that of FIGS. 3 and 4, and that of FIGS. 5 and 6, showing the internal components thereof in greater detail.
Figure 8:
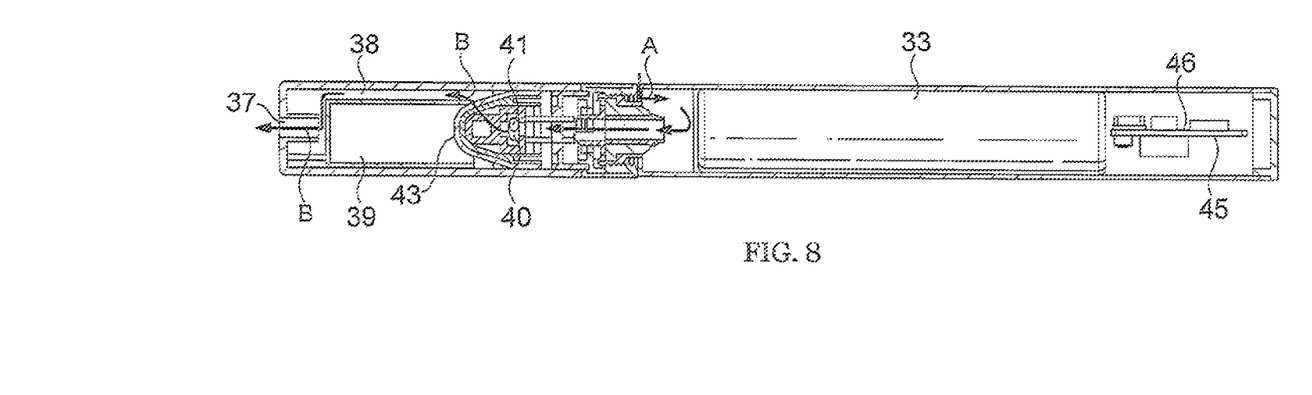
FIG. 8 is a sectional view of the electronic inhalation device of FIG. 7 when assembled.

FIGS. 7 and 8 illustrate another embodiment of an electronic inhalation device in the form of an electronic cigarette. The device is similar to the embodiment shown in FIGS. 3 and 4, and the embodiment shown in FIGS. 5 and 6, although the embodiment in FIGS. 7 and 8 shows the internal components thereof in greater detail. The device comprises a mouthpiece 31, vaporizer device 32 and control unit 33 which can be assembled as shown in FIG. 8 to provide a generally cylindrical device that can be used as a substitute for a conventional tobacco burning cigarette. The control unit 33 is provided with a threaded extension 34 that is received in an interior thread 35 in the vapor device 32. The mouthpiece 31 comprises a generally cylindrical plastics casing 36 that can be push-fitted on to the vapor device 32.

The mouthpiece 31 has an outlet 37 to supply vapor to the mouth of the user and an outlet passageway 38 for the vapor which, in use is produced by the vapor device 32. The mouthpiece 31 also includes a liquid reservoir comprising a porous storage matrix 39 such as plastics open foam material impregnated with a vaporizable liquid, such as a nicotine containing liquid that in use is vaporized by the vapor device 32. The matrix 39 acts as a reservoir for the liquid and since the mouthpiece 31 is readily removable and replaceable, it can be used as a refill capsule when the liquid in the porous matrix 39 becomes depleted and needs to be replenished.

The vapor device 32 includes an electronic heating coil 40 that is wound around a ceramic core 41, supported on a ceramic base 42. A generally U-shaped wicking member 43 is configured to wick liquid from the reservoir 39 towards the heating element 40 by capillary action. The wicking member 43 may for example by made of a metallic foam such as nickel foam.

The heater coil 40 is powered by a rechargeable battery 44 located in the control unit 33 through electrical contacts 48, 49 (not shown in FIGS. 7 and 8, see FIG. 9) which electrically couple the heater coil to the battery 44 when the control unit 33 is fitted to the vapor device 32 by the engagement of threads 34, 35. The electrical power of the battery 44 is supplied to the heater coil 40 under the control of a control circuit 45 mounted on circuit board 46 within the control unit 33.

Figure 9:
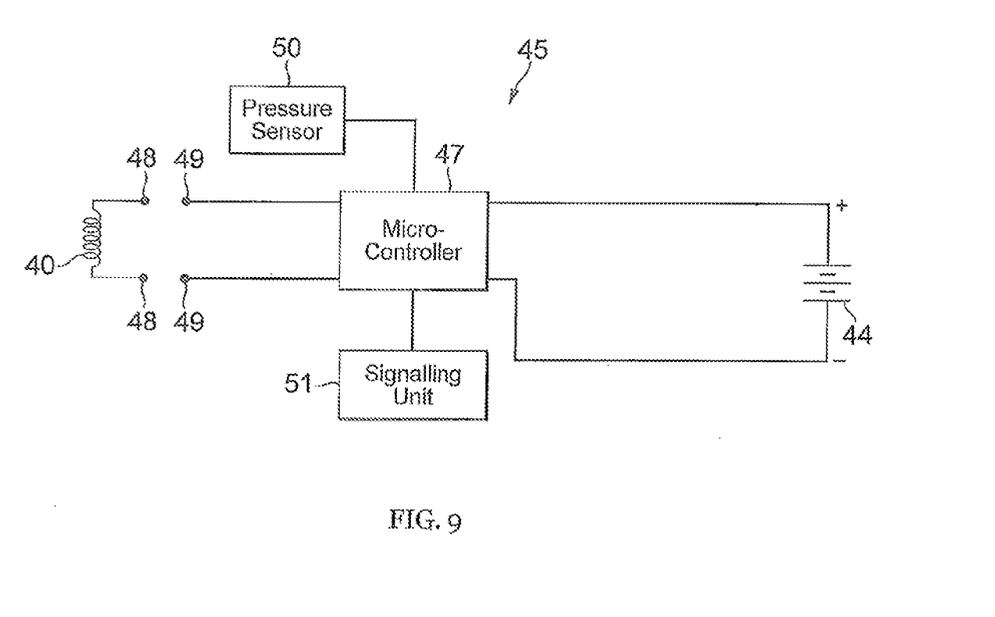
FIG. 9 is a schematic circuit diagram of the electronic inhalation device of FIGS. 7 and 8.

As shown in FIG. 9, the control circuit 45 includes a microcontroller 47 powered by battery 44 to supply an electric heating current to the coil 40 through the contacts 48, 49 that are brought into electrical connection when the control unit 33 is threadedly engaged with the vapor device 32 by means of threads 34, 35 shown in FIG. 7.

A pressure sensor 50 detects when a user draws on the mouthpiece 38, as described in more detail hereinafter.

Also, a signaling unit 51 is provided to provide audio or visual outputs to the user indicative of operational conditions of the device. For example, the signaling device may include a light emitting diode that glows red when the user draws on the device. The signaling device may provide predetermined audio or visual signals to indicate for example that the battery 44 needs to be recharged.

The supply of current from the battery 44 to the mouth controller is controlled by switching transistor 52.

When the user draws on the mouthpiece 1 so as to draw vapor through the outlet 37, the pressure sensor 50 detects the drop in pressure which is communicated from within the vapor device 32 through the interior of the control unit 33 to the circuit board 45. Microcontroller 47 responds to the pressure drop detected by the sensor 50 to supply electrical current to the heater coil 4o, which vaporizes liquid supplied by capillary action through the U-shaped wicking member 43. An air inlet passageway 55 is provided in the joint between the vapor unit 32 and control unit 33 so that air can be drawn through the threaded extension 34 of the control unit 33 into the vapor device 32 in the direction of arrows A, so that the resulting vapor is drawn in the direction of arrows B through passageway 38 to the outlet 37.

The operation of the device of FIGS. 7 and 8 may be the same as that of any of the devices of FIGS. 1 to 6 described previously and so a detailed description of such operation will not be repeated here. However, it is intended that the control circuit 46 of the embodiment of FIGS. 7 and 8 may be configured as per the circuit board 14 of the embodiments of FIGS. 1 to 6, and vice versa. Specifically, the circuit board 46 may comprise a transmitter 18 configured and operable as described previously with respect to the embodiments shown in FIGS. 1 to 6, and so the device may be capable of transmitting usage data and may be activated and/or operated as described previously. Also, the pressure sensor 50 may be disposed on the circuit board 46 within the control unit 33 and the vapor device 32 may be in fluid communication with the area within the control unit 33, via an open passageway for example (not shown), such that a drop in pressure within the vapor device 32 is detectable by a pressure sensor on the circuit board 46 within control unit 33.

In addition to the above, the microcontroller 47 of the embodiment of FIGS. 7 and 8 may be programmed as per the computer 20 of the embodiments of FIGS. 1 to 6 to monitor the measured pressure from the pressure sensor 16 to control the device accordingly and as described previously, particularly to run software to control the operation of the device, including monitor device usage and monitor and calculate the respective usage parameters, as described previously.

The circuit board 46 may further comprise a microphone 26 as per the embodiment shown in FIGS. 3 and 4 and described above, such that the device may act as both a transmitter and a receiver, and function as described in detail above with respect to that particular embodiment.

Although examples have been shown and described it will be appreciated by those skilled in the art that various changes and modifications might be made without departing from the scope of the disclosure. The computer processor could be a microprocessor or a microcontroller. The device is not restricted to being cigarette shaped. The computer processor, transmitter and pressure sensor are not restricted to being on the same circuit board. The heating coil used for vaporization could be replaced by another type of non-coil heating element. The control for the transmitter could be a button or a switch or some other means, rather than the pressure senor or microphone. The use data could store more information such as details relating to each inhalation including date, time and duration In order to address various issues and advance the art, the entirety of this disclosure shows by way of illustration various embodiments in which the claimed invention(s) may be practiced and provide for superior electronic inhalation devices. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilised and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future. Any feature of any embodiment can be used independently of, or in combination with, any other feature.

The invention claimed is:

1. An electronic inhalation device comprising:
   a mouthpiece;
   a control unit, the control unit comprising a power cell and a computer, wherein the computer comprises a computer processor, a memory and an input-output means; and
   a transmitter connected to the computer,
   wherein the computer is configured in use to collect and store data relating to the electronic inhalation device in the computer memory and transmit use data, wherein the transmitter is an audio signalling means and is configured to transmit the use data by sound, wherein the use data comprises at least one of: an inhalation count, wherein the inhalation count is a count of a number of inhalations a user has taken on the electronic inhalation device, an average inhalation time, wherein the average inhalation time is a mean average of the inhalations counted in the inhalation count, or a session count, wherein the session count is a count of a number of inhalation sessions.

2. The electronic inhalation device of claim 1, wherein the electronic inhalation device is an electronic cigarette.

3. The electronic inhalation device of claim 1, wherein the computer is a microcontroller.

4. The electronic inhalation device of claim 1, wherein the transmitter is configured to transmit the use data by wireless means.

5. The electronic inhalation device of claim 1, wherein the inhalation count is stored in 1 byte or 2 bytes of data memory.

6. The electronic inhalation device of claim 1, wherein the average inhalation time is stored in 1 byte or 2 bytes of data memory.

7. The electronic inhalation device of claim 1, wherein the session count is stored in 1 byte or 2 bytes of data memory.

8. The electronic inhalation device of claim 1, wherein an inhalation session ends when the electronic inhalation device is inactive for a predetermined inactivity time following inhalation on the electronic inhalation device.

9. The electronic inhalation device of claim 1, wherein the use data is stored in 8 bytes or less of data memory.

10. The electronic inhalation device of claim 1, wherein the use data is optimized for transmission by sound.

11. The electronic inhalation device of claim 1, wherein the use data further comprises header data at a start of the use data to indicate the start of the use data.

12. The electronic inhalation device of claim 1, wherein the use data further comprises footer data at an end of the data to indicate the end of the data.

13. The electronic inhalation device of claim 1, wherein the use data further comprises configuration data towards a start of the data to indicate how the data is configured for transmission.

14. The electronic inhalation device of claim 13, wherein the configuration data indicates a frequency range of the data transmission or a duration of the data transmission, or an intensity of the data transmission.

15. The electronic inhalation device of claim 1, wherein the use data comprises details of individual inhalation events such as a date and a time of each inhalation, or a duration of each inhalation.

16. The electronic inhalation device of claim 1, wherein the computer is configured in use to transmit the use data at a frequency substantially above a frequency range of typical background noise.

17. The electronic inhalation device of claim 1, wherein the transmitter is a speaker.

* * * * *